(12) United States Patent
Selzer et al.

(10) Patent No.: US 7,851,462 B2
(45) Date of Patent: *Dec. 14, 2010

(54) METHODS AND COMPOSITIONS FOR INHIBITING TUMOR GROWTH

(75) Inventors: Edgar Selzer, St. Andrä-Wördern (AT); Burkhard Jansen, La Jolla, CA (US); Reinhard Paschke, Halle (DE)

(73) Assignee: Novelix Pharmaceuticals, Inc., La Jolla, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 11/963,505

(22) Filed: Dec. 21, 2007

(65) Prior Publication Data

US 2008/0214516 A1 Sep. 4, 2008

Related U.S. Application Data

(63) Continuation of application No. 10/545,143, filed as application No. PCT/AT2004/000045 on Feb. 11, 2004, now Pat. No. 7,312,205.

(30) Foreign Application Priority Data

Feb. 11, 2003 (AT) ................. A 200/2003

(51) Int. Cl.
*A61K 31/56* (2006.01)
*C07J 53/00* (2006.01)
(52) U.S. Cl. ...................... 514/169; 552/510
(58) Field of Classification Search .......... 514/169; 552/510
See application file for complete search history.

(56) References Cited

U.S. PATENT DOCUMENTS

| 5,962,527 A | 10/1999 | Pezzuto et al. ............... 514/569 |
| 2002/0052352 A1 | 5/2002 | Pezzuto et al. ............... 514/182 |

FOREIGN PATENT DOCUMENTS

| EP | 0 943 620 | 9/1999 |
| WO | WO 96/29068 | 9/1996 |
| WO | WO 00/24762 | 5/2000 |
| WO | WO 00/46235 | 8/2000 |
| WO | WO 01/18029 | 3/2001 |
| WO | WO 02/091858 | 11/2002 |

OTHER PUBLICATIONS

Greene and Wuts, "Chapter 2: Protection for the Hydroxyl Group, Including 1,2- and 1,3-Diols," In: Protective Groups in Organic Synthesis $3^{rd}$ Ed., John Wiley & Sons, Inc., pp. 17-245, 1999.
Greene and Wuts, "Chapter 7: Protection for the Amino Group," In: Protective Groups in Organic Synthesis $3^{rd}$ Ed., John Wiley & Sons, Inc., pp. 494-653, 1999.
Sigma, Cat. No. H-107, 2006.
Sigma, Cat. No. H-125, 2006.
Wermuth, "The Practice of Medicinal Chemistry," Academic Press, San Diego CA, pp. 756-776, 1996.
Willmann et al., "Characterization of NVX-207, a novel betulinic acid-derived anti-cancer compound," *European Journal of Clinical Investigation*, 39:384-94, 2009.

*Primary Examiner*—Barbara P Badio
(74) *Attorney, Agent, or Firm*—Fulbright & Jaworski LLP (57) ABSTRACT

The present invention relates to novel betulinic acid derivatives with increased activity for the treatment of carcinomas and HIV diseases, a method for preparing such novel betulinic acid derivatives as well as their use as pharmaceuticals.

19 Claims, 2 Drawing Sheets

METHODS AND COMPOSITIONS FOR INHIBITING TUMOR GROWTH

This application is a continuation of U.S. application Ser. No. 10/545,143, filed Aug. 10, 2005, now U.S. Pat. No. 7,312,205, which is a national phase application under 35 U.S.C. §371 of International Application No. PCT/AT2004/000045 filed 11 Feb. 2004, which claims priority to Austrian Application No. A 200/2003 filed 11 Feb. 2003. The entire texts of each of the above-referenced disclosures are specifically incorporated herein by reference.

BACKGROUND OF THE INVENTION

Field of the Invention

The present invention relates to novel betulinic acid derivatives with increased activity for the treatment of carcinomas and HIV diseases, a method for preparing such novel betulinic acid derivatives as well as their use as pharmaceuticals. Like betulinic acid, the compounds according to the invention are suitable for clinical use in men and animals to inhibit the growth of various tumors (melanomas, sarcomas, lymphomas, squamous carcinomas and other tumors mentioned below) as well as for the treatment of HIV diseases and—due to their antiphlogistic activity—unspecific inflammatory diseases.

SUMMARY OF THE INVENTION

The invention relates to novel betulic acid derivatives having the general formula (I)

wherein $R_1$ represents a hydroxy group, an amino group, a protected hydroxy group or a protected amino group. Suitable protective groups are known from the prior art, e.g., from Chapters 2 and 7 of "Protective Groups in Organic Synthesis", T. W. Greene and P. G. M. Wuts, 3$^{rd}$ Edition, John Wiley & Sons, Inc. (1999), that disclosure, thus, being incorporated in the present description by reference;

and $R_2 =$

In particular, the present invention relates to novel betulic acid derivatives having the general formula (I) as indicated above, wherein $R_1$ represents a hydroxy group, an amino group or one of the following protected hydroxy or amino groups:

and $R_2$ is as defined above.

The compounds according to the invention are novel betulic acid derivatives with increased activity and better solubility in polar solvents, and hence markedly improved application options. It goes without saying that any possible salts and inclusion compounds of the compound according to the invention are covered by the aforementioned definition of general formula (I).

The present invention further relates to a method for preparing compounds of the general formula (I), wherein a betulic acid halide, particularly a betulic acid chloride, appropriately protected by the substituent $R_1$ is reacted with an alcohol or amine appropriately substituted to provide the substituent $R_2$. If desired, the thus obtained compound of the general formula (I) wherein $R_1$ represents a protected hydroxy or amino group may then be deprotected, by measures known from the prior art, as a function of the selected protective group to provide a compound of the general formula (I) wherein $R_1$ represents hydroxy or amino.

The natural substance betulic acid, which serves as the starting and comparative compound for the compounds according to the invention, is a triterpene that was isolated already at the beginning of the last century. The name is derived from the respective alcohol betulin, an ingredient of birch bark, where it occurs in large quantities. Betulic acid exhibits anti-malaria, anti-inflammatory, anti-HIV and anti-tumor effects, which have been described in a great number of different publications. Used as a chemotherapeutic, betulic acid induces the so-called programmed cell death, also referred to as apoptosis, in tumor cells of various origins (e.g., melanoma cells). In melanomas, antiproliferative effects were detected in human mouse models both in vitro and in vivo. Particularly in melanoma cells, betulic acid appears to specifically induce an apoptotic cell destruction in tumor cells, while melanocytes are largely resistant to this substance. To date, hardly any data on possible synergistic effects between betulic acid and other cytostatics have been available. The molecular action mechanisms in infantile tumors (Ewing sarcoma, medulloblastoma) as well as in glioblastomas were particularly well investigated by the research group around S. Fulda (children's hospital, Ulm).

Other known effects of betulic acid and its known derivatives, which have been well documented in the scientific literature, include its activity against HIV viruses, whose replication and receptor binding they are able to suppress, as well as their anti-inflammatory activity, which is, for instance, described by way of a mouse-ear inflammation model. Due to its antiproliferative action against various tumors (melanomas, neuroectodermal tumors, sarcomas), which has been described both in animal experiments and in cell cultures, betulic acid is, thus, an extremely interesting substance for both single and possible combination therapies with other cytostatically active substances and cell-death-modulating substances, e.g., antisense oligonucleotides against various anti-apoptotic Bcl-2 family members and, in particular, Bcl-2, Bcl-xL as well as Mcl-1.

Publications on the action mechanism of betulic acid primarily in melanomas as well as with Ewing sarcoma, glioblastoma and medulloblastoma have demonstrated that its effects are to a substantial extent caused by the induction of apoptosis on a mitochondrial level. It is still unclear today what primary points of attack it has within the cell; amongst others neither any binding sites (receptors), if present, nor the initial signal pathways have been sufficiently explored. However, the inventors and other authors were able to demonstrate that betulic acid induces apoptosis in malign cells, yet human melanocytes and even normal cells appear to be less sensitive than malign cells. That observation is of interest, above all, also because animal-experimental data in mice have not revealed any remarkable toxicity. Apart from those data acquired in cell cultures there are clues to the effect that betulic acid is more strongly concentrated in tumor tissues than in normal tissues. The induction of various Bcl-2 family members both in melanoma cells and in normal melanocytes and in sarcoma lines were investigated too. It was found that the expression of the anti-apoptotic protein Mcl-1 can be induced within a few hours by betulic acid. The other examined proteins of this gene family, above all Bcl-2 and Bcl-x, as well as the expression of the p53 protein remained unchanged under that treatment. The data from the scientific literature have indicated that the effects of betulic acid do not depend on the p53 protein. Since it has been recently shown that Bcl-2 and Bcl-xL are able to inhibit betulic-acid-induced apoptosis, these observations suggest a combination of betulic acid with Bcl-2 and/or Bcl-xL antagonization, e.g., by antisensoligonucleotide (ASO). The same considerations apply to possible combinations with, e.g., Mcl-1 ASOs. A property of betulic acid of potential clinical relevance is the recent observation that its cytotoxicity is enhanced in low-pH culture medium. The pH is in many tumors lower than in normal tissues (Noda Y. et al, 1997). The same authors found that betulic acid is more active against resting cells than against cells in their growth phases. This property might be of additional relevance in clinical use, since many chemotherapeutics as well as radiotherapy are less effective against resting and/or acidotic cell populations.

At present, melanomas, neuroectodermal tumors as well as sarcomas and HIV have above all been the most intensively investigated. These are tumors which are particularly difficult to treat and of which primarily the generalized disease forms offer hardly promising treatment options. In patients suffering from metastasized melanomas, therapeutical options are largely limited to a few substances. These include 5-(3,3-dimethyl-2-triazenyl)-1-H-imidazole-4-carboxamide (Dacarbazine, DTIC). Dacarbazine still constitutes the most effective monotherapy in melanoma, exhibiting response rates in the order of about 30%. Combination therapies with other synthetic or recombinant substances, e.g., BCNU, Cisplatine, Tamoxifen, Interferon-alpha and Interleukin-2 show higher response rates in some clinical studies. These are, however, limited in time and entail elevated toxicities. Some substances derived from natural products such as, e.g., Adriamycin, Bleomycin, Etoposide and others have been investigated in respect to their activities against melanomas and their toxicities. However, in the end none of these substances turned out to be convincing in clinical daily routine.

DESCRIPTION OF ILLUSTRATIVE EXAMPLES

In the following, the method according to the invention will be explained in more detail by way of some examples, whereby the disclosure of the invention is not limited to these examples.

1) Acetyl betulic acid-2-amino-3-hydroxy-2-hydroxymethyl propyl ester IV (Compound B)

Reaction Scheme 1:

IV

The synthesis of acetyl betulic acid-2-amino-3-hydroxy-2-hydroxymethyl propyl ester IV is performed by departing from betulic acid I via the intermediate stages of acetyl betulic acid II and the respective acid chloride III, by reacting the acid chloride III with trishydroxymethylaminomethane.

a) Acetyl betulic acid (MW 498.74) II

Two grams of betulic acid I (MW 456.70) in 50 ml acetic anhydride are heated at reflux for 2 hours. After cooling, the reaction is poured into ice water under vigorous stirring, filtered, and the obtained solid is washed with water until the acetic acid smell has disappeared.

The solid is then heated at reflux in 70% ethanol for 4 hours under stirring.

After cooling, the reaction solution is filtered, the mother liquor is slightly concentrated, cooled in an ice bath and filtered once again. Yield: 86%; mp.: 290° C.

b) Acetyl betulic acid chloride (MW 517.18) III

Two grams of acetyl betulic acid II are provided in dry benzene and supplemented with a 10-fold excess of oxalyl chloride (3.4 ml). The reaction mixture is stirred for 8 hours under cooling, and the solvent as well as excess oxalyl chloride are subsequently evaporated on a rotary evaporator. In order to remove any oxalyl chloride residues, another 20 ml of benzene are added and again evaporated under vacuum.

c) Acetyl betulic acid-2-amino-3-hydroxy-2-hydroxymethyl propyl ester (MW 601.86) IV, (Compound B)

The acid chloride obtained from 1 g acetyl betulic acid (about 0.002 mol) by the method according to b) is reacted without further purification. To this end, it is dissolved in 35 ml dioxan (dry), and tris(hydroxymethyl)-aminomethane is added in double excess (0.004 mol, 0.5 g). After the addition of a spatula tip of DMAP and 3 drops of pyridine, the reaction mixture is stirred for 2 days at room temperature.

After this, the solids are filtered off, the solution is concentrated on the rotary evaporator and taken up in chloroform. This chloroform solution is washed free of pyridine with 1% hydrochloric acid, water and saturated saline solution several times. After drying over $Na_2SO_4$, the solvent is removed and the product is purified over a silica gel column or (and) chromatotron. A chloroform-methanol mixture at a ratio of 10:1 was used as an eluant. Yield: 20%, mp: 156° C.

2) Acetyl betulic acid-N-(1,1-bis(hydroxymethyl)-2-hydroxyethyl)formamide (MW 601.86), (Compound C)

The synthesis of acetyl betulinic acid N-(1,1-bis(hydroxymethyl)-2-hydroxyethyl)formamide (compound C) is carried out in a manner analogous to reaction scheme 1, departing from betulic acid I via the intermediate stages of acetyl betulic acid II and the respective acid chloride III, by reacting the acid chloride III with tris(hydroxymethyl)aminomethane.

The acid chloride obtained from 1 g acetyl betulic acid (about 0.002 mol) according to the method of 1)b) is reacted without further purification. To this end, it is dissolved in 35 ml anhydrous dioxan, and an equimolar amount of tris-(hydroxymethyl)aminomethane (0.002 mol, 0.25 g) is added. After the addition of a spatula tip of DMAP and 3 drops of pyridine, the reaction mixture is heated to 80° C. for 8 hrs. After this, the reaction solution is concentrated on the rotary evaporator and the residue is taken up in chloroform. This chloroform solution is washed free of pyridine with 1% hydrochloric acid, water and saturated saline solution several times. After drying over $Na_2SO_4$, the solvent is removed and the product is purified over a silica gel column or (and) chromatotron. A chloroform-methanol mixture at a ratio of 10:1 was used as an eluant. Yield: 15%, mp: 184° C.

In the following, the use of the compounds according to the invention for the inhibition of tumor growths are described in comparison to betulic acid (comparative compound A).

Growth Inhibition in Various Tumor Lines

Figure 1:
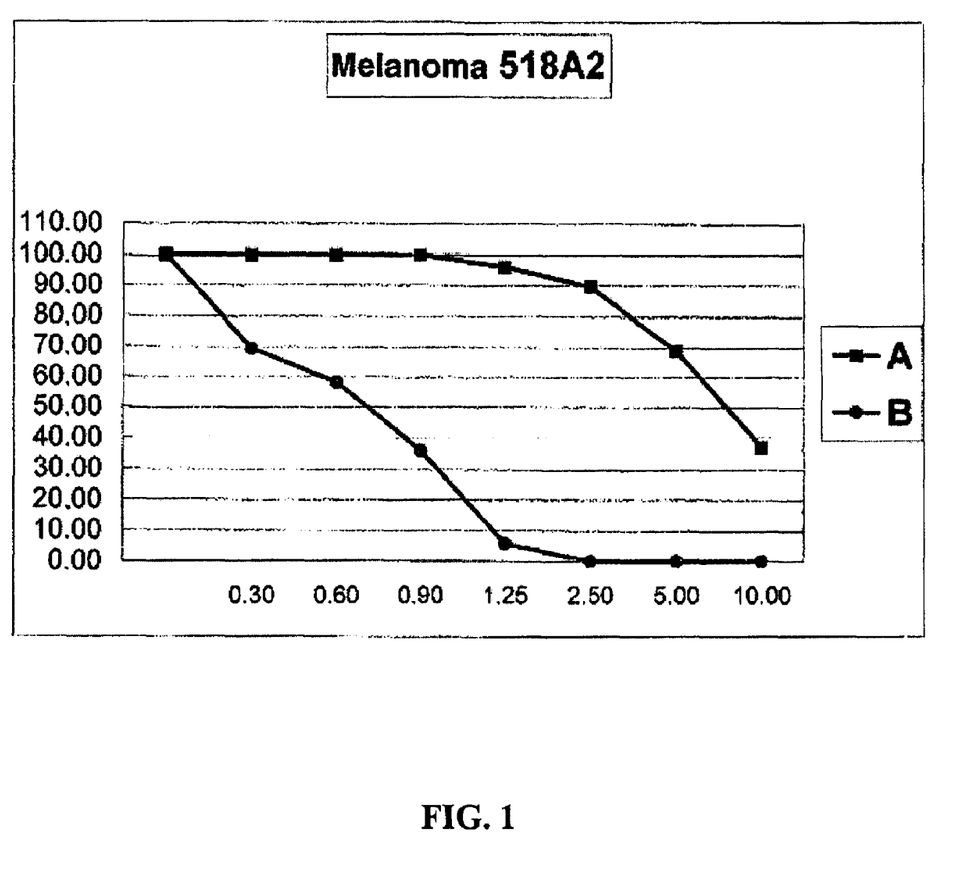
FIG. 1 shows a comparison of the growth inhibition of melanoma cell line 518A2 by compound A (betulic acid) and compound B (protected betulic acid triester) after 48 hours. The x-axis indicates the concentration in μg/ml of compounds A and B. The Y-axis gives the cell survival rate as a percentage of the untreated controls.
Figure 2:
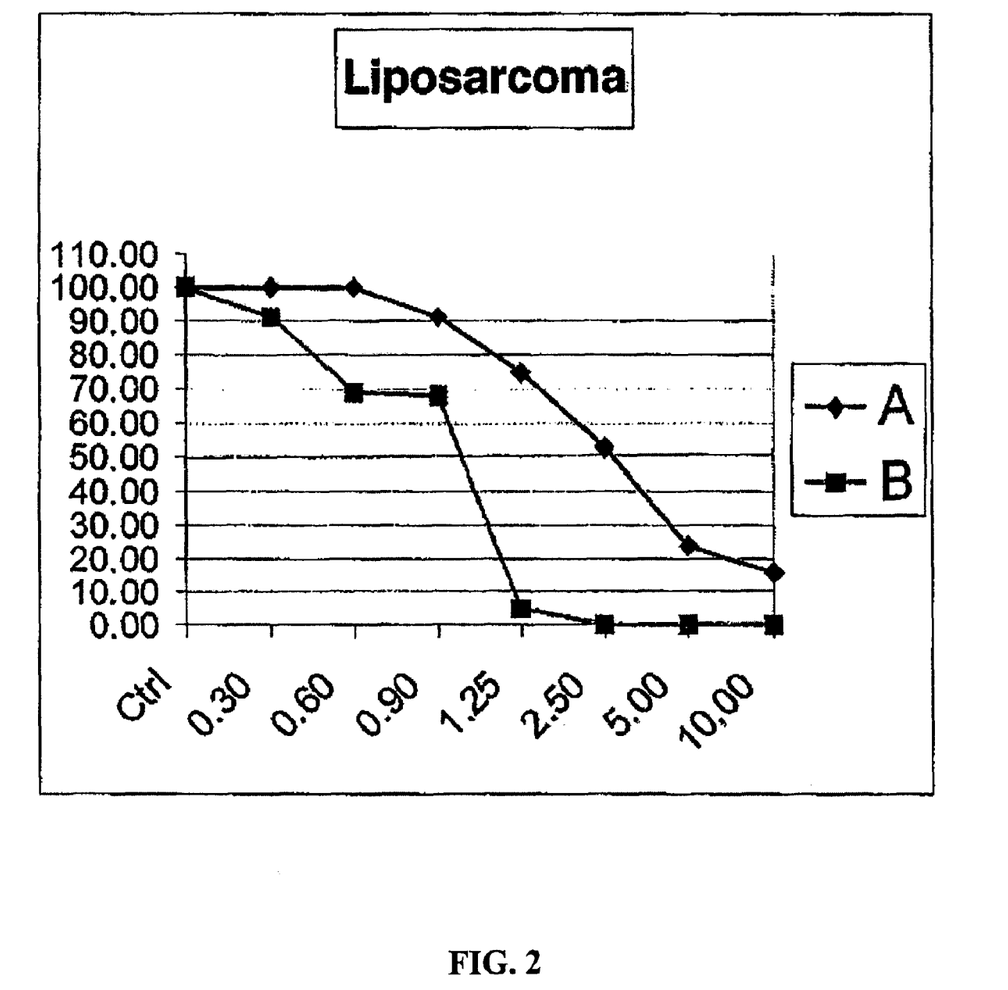
FIG. 2 shows a comparison of the growth inhibition of a liposarcoma cell line (ATCC HTB-92) by compound A (betulic acid) and compound B (protected betulic acid triester) after 48 hours. The x-axis indicates the concentration in μg/ml of compounds A and B. The Y-axis gives the cell survival rate as a percentage of the untreated controls.

Examples 1 and 2 show direct comparisons between comparative compound A (betulic acid) and a novel derivative (compound B) in paired growth assays (cell count decrease after 3 days after a single application of the indicated concentrations of the respective compounds on day 1).

EXAMPLE 1

Comparison of compound (A) (betulic acid) with compound (B) (protected betulic acid trimester)—Growth inhibition in melanoma cell line 518A2 (obtained from Peter Schrier, Leiden, The Netherlands) after 48 hrs. The X-axis indicates the concentration in µg/ml of compounds A and B, respectively, the Y-axis gives the cell survival rate in percent of the untreated controls.

The $ED_{50}$ for comparative compound (A) is about 5 µg/ml, that for compound (B) about 0.7 µg/ml.

Compound (B):

Compound (B), thus, exhibits a clearly higher activity than comparative compound (A), i.e., up to 7 times higher.

A similarly enhanced activity is also observed with sarcomas, as shown below by way of examples on a cell line.

EXAMPLE 2

Comparison of the efficacy of comparative compound (A) (betulic acid) with that of compound (B) (protected betulic acid trisester) in a liposarcoma line (ATCC HTB-92). The X-axis indicates the concentration in µg/ml of compounds A and B, respectively, the Y-axis gives the cell survival rate in percent of the untreated controls.

The $ED_{50}$ for comparative compound (A) is about 2.5 µg/ml, that for compound (B) is about 0.9 µg/ml.

EXAMPLE 3

Comparison of the effects of different betulic acid derivatives according to the invention and of the comparative compound (betulic acid), respectively, on various melanoma-sarcoma lines. The data each refer to cell survival rates in percent (mean values) as against untreated cell cultures.

3a) Comparative Compound (A) (betulic Acid)—Effect on Liposarcoma Line ATCC HTB-92

| Conc. µg/ml | survival in % |
| --- | --- |
| 0.3 | 98.0 |
| 0.6 | 92.8 |
| 1 | 92.3 |
| 1.25 | 79.5 |
| 2.5 | 49.3 |
| 5 | 20.8 |
| 10 | 15.7 |

3b) Compound (B) (Protected Betulic Acid Trisester)—Effect on Liposarcoma Line ATCC HTB-92

| Conc. µg/ml | survival in % |
| --- | --- |
| 0.3 | 89.5 |
| 0.6 | 70.7 |
| 1 | 12.0 |
| 1.25 | 2.9 |

-continued

| Conc. µg/ml | survival in % |
|---|---|
| 2.5 | 3.0 |
| 5 | 0.0 |
| 10 | 0.0 |

3c) Compound (B) (Protected Betulic Acid Trisester)—Effect on Melanoma Line 518A2

| Conc. µg/ml | survival in % |
|---|---|
| 0.3 | 83.0 |
| 0.6 | 56.3 |
| 1 | 11.3 |
| 1.25 | 10.3 |
| 2.5 | 2.8 |
| 5 | 0.0 |
| 10 | 0.0 |

3d) Compound (C) (Protected Betulic Acid Trisester)—Effect on Melanoma Line 518A2 and Liposarcoma Line ATCC HTB-92

Compound (C):

| Conc. µg/ml | survival in % melanoma |
|---|---|
| 0.25 | 96 |
| 0.5 | 93 |
| 1 | 67.5 |

| Conc. µg/ml | survival in % liposarcoma |
|---|---|
| 0.3 | 96 |
| 0.6 | 82 |
| 1.0 | 81 |

EXAMPLE 4

Preparation of a inclusion compound comprising compound (B) (protected betulinic acid trisester) in HBC (2-hydroxpropyl-beta-cyclodextrin, Sigma, Cat. No. H-107) or in HGC (2-hydroxypropyl-gamma-cyclodextrin, Sigma, Cat. No. H-125).

Compound (B):

The respective stock solutions for further dilution are indicated below. Fifty or 100 mg/ml of compound (B) were each dissolved in EtOH. HBC was separately dissolved in water or in water plus EtOH. The further mode of procedure was basically the same as described in the data sheet supplied by Sigma. No attempts were made to adjust the pH. The solubility of compound (B) in aqueous solutions by means of inclusion in HBC or similar compounds definitely remains to be further improved, e.g., in gamma-cyclodextrin.

| Test #1: | compound (B) | 50 mg/ml in EtOH dissolved as usual |
|---|---|---|
| Test #2: | compound (B) | 5.9 mg/ml in 266 mg/ml HBC in $H_2O$ |
| Test #3: | compound (B) | 20 mg/ml in 266 mg/ml HBC in 50% EtOH/ 50% $H_2O$ |
| Test #4: | compound (B) | 25 mg/ml in 200 mg/ml HGC in 50% EtOH/ 50% $H_2O$ |

The stock solutions indicated above were diluted to 1 mg/ml in EtOH and subsequently directly added to the culture medium.

4a) Compound (B) (Protected Betulinic Acid Trisester) as Inclusion Compound in HBC (2-hydroxpropyl-beta-cyclodextrin) or in HGC (2-hydroxypropyl-gamma-cyclodextrin)—Effect on Melanoma Line 518A2

Survival in percent as with all other data after 3 days of cell culture after a single application on day 1

| Conc. µg/ml | Survival in % melanoma |
|---|---|
| Test #1 | |
| 1.0 | 50 |
| 2.0 | 0.5 |
| 3.0 | 0.0 |
| 4.0 | 0.0 |
| Test #2 | |
| 1.0 | 65 |
| 2.0 | 25 |
| 3.0 | 0.0 |
| 4.0 | 0.0 |
| Test #3 | |
| 1.0 | 77 |
| 2.0 | 24 |
| 3.0 | 0.0 |
| 4.0 | 0.0 |

-continued

| Conc. µg/ml | Survival in % melanoma |
|---|---|
| Test #4 | |
| 1.0 | 59 |
| 2.0 | 4 |
| 3.0 | 0.0 |

4b) Tolerance of Compound (B) (Protected Betulinic Acid Trisester) as Inclusion Compound in HGC (2-hydroxypropyl-gamma-cyclodextrin) in a Mouse Model Methodology: A HGC/compound (B) complex dissolved in water was intravenously injected into the tail vein of pathogen-free female C.B.-17 scid/scid (SCID) mice (4-6 weeks old, Harlan Winkelmann, Borchen, Germany). The inclusion compound was prepared as described in Example 4. The alcohol portion was removed by freezedrying of the mixture and subsequent reconstitution in water. The total volume per injection for the experiments indicated below was 200 µl.

Test #1

Initially, two mice were each treated with 100 µg HGC/compound (B) complex three times in a row on every third day. In case of good tolerance, the next pair of mice was treated with the next higher dose as indicated in the scheme below.

Scheme:
Group A: 3 times 100 µg HGC/compound (B) complex
Group B 3 times 200 µg HGC/compound (B) complex
Group C 3 times 400 µg HGC/compound (B) complex, then continuation with group A treated first:
Group A 3 times 800 µg HGC/compound (B) complex
Group B 3 times 1500 µg HGC/compound (B) complex; then discontinuation because of local irritation phenomena.

The tests were discontinued at 1500 µg HGC/compound (B) complex because of strong local irritation phenomena in one of two mice, yet without any apparent systemic toxicity. Overall, an amount of 800 µg HGC/compound (B) complex could be administered per injection per mouse without apparent toxicity. At higher concentrations (about >1.5 mg HGC/compound (B) complex per mouse), local irritation phenomena were observed. It is conceivable that slower infusion rates may help avoid such side effects.

Test #2
In a test group of 3 mice, 800 µg HGC/compound (B) complex (in 200 µl volume) was each administered per mouse every third day, six times in a row. Also this showed no apparent clinically toxic effects. The subsequent autopsy did not suggest any macroscopic organ changes.

The invention claimed is:

1. A betulinic acid derivative, salt, or inclusion compound having a formula (I):

wherein $R_1$ is a hydroxy group, an amino group, a protected hydroxy group, or a protected amino group; and
$R_2$ is one of:

2. The compound of claim 1, wherein $R_1$ is one of the following:

3. The compound of claim 1, wherein the compound has the formula:

4. The compound of claim 1, wherein the compound has the formula:

5. A pharmaceutical composition comprising a compound of claim 1.

6. A method of treating cancer in a mammal comprising administering to the mammal an effective amount of a betulinic acid derivative, salt, or inclusion compound having a formula (I):

wherein $R_1$ is a hydroxy group, an amino group, a protected hydroxy group, or a protected amino group; and $R_2$ is one of:

-continued wherein the cancer in the mammal is treated.

7. The method of claim 6, wherein $R_1$ is one of the following:

8. The method of claim 6, wherein the cancer is a squamous carcinoma.

9. The method of claim 6, further comprising administering to the mammal a cytostatically active substance and/or a cell-death-modulating substance.

10. The method of claim 9, wherein the cell-death-modulating substance is an antisense oligonucleotide against an anti-apoptotic Bcl-2 family member or Mcl-1.

11. The method of claim 10, wherein the Bcl-2 family member is Bcl-2 or Bcl-xL.

12. A method of treating HIV disease in a mammal comprising administering to the mammal an effective amount of a betulinic acid derivative, salt, or inclusion compound having a formula (I):

wherein $R_1$ is a hydroxy group, an amino group, a protected hydroxy group, or a protected amino group; and
$R_2$ is one of:

wherein the cancer in the mammal is treated.

13. The method of claim 12, wherein $R_1$ is one of the following:

14. The method of claim 6, wherein $R_2$ is:

15. The method of claim 6, wherein $R_2$ is:

16. The method of claim 12, wherein $R_2$ is:

17. The method of claim 12, wherein $R_2$ is:

18. The method of claim 12, wherein the compound has the formula:

19. The method of claim 12, wherein the compound has the formula:

* * * * *

UNITED STATES PATENT AND TRADEMARK OFFICE
CERTIFICATE OF CORRECTION

PATENT NO.       : 7,851,462 B2
APPLICATION NO.  : 11/963505
DATED            : December 14, 2010
INVENTOR(S)      : Edgar Selzer et al.

It is certified that error appears in the above-identified patent and that said Letters Patent is hereby corrected as shown below:

In claim 1, column 12, lines 25-33, delete second chemical drawing and insert

-- therefor.

Signed and Sealed this
Fifteenth Day of March, 2011

David J. Kappos
*Director of the United States Patent and Trademark Office*